(12) United States Patent
Garcia Da Fonseca et al.

(10) Patent No.: US 9,013,704 B2
(45) Date of Patent: Apr. 21, 2015

(54) SURFACE PLASMON RESONANCE DETECTION SYSTEM

(75) Inventors: João Garcia Da Fonseca, Azambuja (PT); João Dias Pedro Nicolau Manso, Oeiras (PT); Pedro Miguel Monteiro Gomes, Amadora (PT); Sandro Miguel Pinto Bordeira, Odivelas (PT); José Pedro Santos Manso Côrte-Real, Lisboa (PT)

(73) Assignee: Biosurfit, S.A., Aveiro (PT)

( * ) Notice: Subject to any disclaimer, the term of this patent is extended or adjusted under 35 U.S.C. 154(b) by 253 days.

(21) Appl. No.: 13/518,639

(22) PCT Filed: Dec. 7, 2010

(86) PCT No.: PCT/PT2010/000055
§ 371 (c)(1),
(2), (4) Date: Oct. 15, 2012

(87) PCT Pub. No.: WO2011/078713
PCT Pub. Date: Jun. 30, 2011

(65) Prior Publication Data
US 2013/0027688 A1    Jan. 31, 2013

(30) Foreign Application Priority Data

Dec. 22, 2009 (GB) .................................. 0922440.3

(51) Int. Cl.
| | | |
|---|---|---|
| G01N 21/55 | (2014.01) | |
| G01N 21/552 | (2014.01) | |
| B01L 3/00 | (2006.01) | |
| G01N 21/07 | (2006.01) | |

(Continued)

(52) U.S. Cl.
CPC ............ *G01N 21/553* (2013.01); *B01L 3/5027* (2013.01); *B01L 2300/0803* (2013.01); *B01L 2300/0816* (2013.01); *B01L 2300/168* (2013.01); *G01N 21/07* (2013.01); *G01N 21/253* (2013.01); *G01N 33/54373* (2013.01); *G01N 35/00069* (2013.01)

(58) Field of Classification Search
None
See application file for complete search history.

(56) References Cited

U.S. PATENT DOCUMENTS

| | | |
|---|---|---|
| 5,087,532 A | 2/1992 | Challener, IV |
| 5,414,678 A | 5/1995 | Challener, IV |

(Continued)

FOREIGN PATENT DOCUMENTS

| | | |
|---|---|---|
| DE | 102005048233 | 4/2007 |
| EP | 0608006 | 7/1994 |

(Continued)

OTHER PUBLICATIONS

Notification of Reasons for Refusal for Japanese Application No. 2011-543549, dispatch date May 7, 2013.

(Continued)

*Primary Examiner* — Kara E Geisel
*Assistant Examiner* — Amanda Merlino
(74) *Attorney, Agent, or Firm* — Patteson Thuente Pedersen, P.A.

(57) ABSTRACT

A system for detecting the presence of an analyte in a moving substrate or sample handling device is disclosed, providing means (26,30) for integrated triggering of data acquisition with a detector means (28) and data acquisition with a detector means (28). In particular, a surface Plasmon resonance "lab on disk" reader system is disclosed.

19 Claims, 4 Drawing Sheets

(51) Int. Cl.
  *G01N 21/25*    (2006.01)
  *G01N 33/543*   (2006.01)
  *G01N 35/00*    (2006.01)

(56) References Cited

U.S. PATENT DOCUMENTS

| | | | |
|---|---|---|---|
| 5,508,982 A | 4/1996 | Challener, IV | |
| 5,620,792 A | 4/1997 | Challener, IV | |
| 5,639,567 A | 6/1997 | Challener, IV | |
| 5,751,482 A | 5/1998 | Challener, IV | |
| 5,925,878 A | 7/1999 | Challener | |
| 5,955,378 A | 9/1999 | Challener | |
| 5,986,762 A | 11/1999 | Challener | |
| 5,986,997 A | 11/1999 | Challener, IV | |
| 5,994,150 A | 11/1999 | Challener et al. | |
| 6,030,581 A | 2/2000 | Virtanen | |
| 6,063,589 A | 5/2000 | Kellogg et al. | |
| 6,100,991 A | 8/2000 | Challener | |
| 6,230,991 B1 | 5/2001 | Steinruck et al. | |
| 6,235,531 B1 | 5/2001 | Kopf-Sill et al. | |
| 6,277,653 B1 | 8/2001 | Challener et al. | |
| 6,320,991 B1 | 11/2001 | Challener et al. | |
| RE37,473 E | 12/2001 | Challener | |
| 6,344,490 B1 | 2/2002 | Degeorge et al. | |
| 6,625,336 B2 | 9/2003 | Challener et al. | |
| 6,632,399 B1 | 10/2003 | Kellogg et al. | |
| 6,653,152 B2 | 11/2003 | Challener | |
| 6,944,101 B2 | 9/2005 | Johns et al. | |
| 6,944,112 B2 | 9/2005 | Challener | |
| 7,027,700 B2 | 4/2006 | Challener | |
| 7,106,935 B2 | 9/2006 | Challener | |
| 7,266,268 B2 | 9/2007 | Challener et al. | |
| 7,272,102 B2 | 9/2007 | Challener | |
| 7,275,858 B2 | 10/2007 | Andersson et al. | |
| 7,330,404 B2 | 2/2008 | Peng et al. | |
| 7,412,143 B2 | 8/2008 | Rottmayer et al. | |
| 7,440,660 B1 | 10/2008 | Jin et al. | |
| 7,480,214 B2 | 1/2009 | Challener et al. | |
| 7,515,372 B2 | 4/2009 | Erden et al. | |
| 7,580,602 B2 | 8/2009 | Itagi et al. | |
| 7,768,657 B2 | 8/2010 | Jin et al. | |
| 7,796,487 B2 | 9/2010 | Chu et al. | |
| 7,804,656 B2 | 9/2010 | Gomez et al. | |
| 7,830,775 B2 | 11/2010 | Karns et al. | |
| 7,869,162 B2 | 1/2011 | Lu et al. | |
| 7,869,309 B2 | 1/2011 | Mihalcea et al. | |
| 7,893,497 B2 | 2/2011 | Takasu | |
| 8,440,147 B2 | 5/2013 | Da Fonseca et al. | |
| 2001/0031503 A1 | 10/2001 | Challener et al. | |
| 2002/0122364 A1* | 9/2002 | Worthington et al. | 369/47.35 |
| 2003/0053934 A1 | 3/2003 | Andersson et al. | |
| 2003/0128633 A1 | 7/2003 | Batra et al. | |
| 2003/0137772 A1 | 7/2003 | Challener | |
| 2003/0219713 A1 | 11/2003 | Valencia et al. | |
| 2004/0053290 A1 | 3/2004 | Terbrueggen et al. | |
| 2004/0240327 A1 | 12/2004 | Sendur et al. | |
| 2005/0157597 A1 | 7/2005 | Sendur et al. | |
| 2005/0179901 A1 | 8/2005 | Ostlin et al. | |
| 2005/0217741 A1 | 10/2005 | Bohm | |
| 2006/0187459 A1 | 8/2006 | Ok et al. | |
| 2006/0233061 A1 | 10/2006 | Rausch et al. | |
| 2007/0115787 A1 | 5/2007 | Itagi et al. | |
| 2007/0125942 A1 | 6/2007 | Kido | |
| 2007/0262034 A1 | 11/2007 | Ducree et al. | |
| 2008/0019875 A1 | 1/2008 | Shiga | |
| 2008/0144802 A1 | 6/2008 | Kitawaki et al. | |
| 2008/0149190 A1 | 6/2008 | Bedingham et al. | |
| 2008/0170319 A1 | 7/2008 | Seigler et al. | |
| 2009/0120504 A1 | 5/2009 | Andersson et al. | |
| 2009/0207519 A1 | 8/2009 | Erden et al. | |
| 2009/0208171 A1 | 8/2009 | Gage et al. | |
| 2010/0021347 A1 | 1/2010 | Da Fonseca | |
| 2010/0097901 A1 | 4/2010 | Challener et al. | |
| 2010/0123965 A1 | 5/2010 | Lee et al. | |
| 2011/0044147 A1 | 2/2011 | Karns et al. | |
| 2011/0290718 A1 | 12/2011 | Da Fonseca et al. | |
| 2012/0021447 A1 | 1/2012 | Da Fonseca et al. | |
| 2013/0027688 A1 | 1/2013 | Da Fonseca et al. | |
| 2013/0074962 A1 | 3/2013 | Da Fonseca et al. | |
| 2014/0109972 A1 | 4/2014 | Da Fonseca et al. | |

FOREIGN PATENT DOCUMENTS

| | | |
|---|---|---|
| EP | 1684063 | 7/2006 |
| EP | 1900433 | 3/2008 |
| EP | 2080554 | 7/2009 |
| JP | 02-280084 | 11/1990 |
| JP | 2004117048 | 4/2004 |
| JP | 2005516211 | 6/2005 |
| JP | 2005531757 | 10/2005 |
| WO | WO95/33986 | 12/1995 |
| WO | WO9708556 | 3/1997 |
| WO | WO97/21090 | 6/1997 |
| WO | WO0146465 | 6/2001 |
| WO | WO03/058641 | 7/2003 |
| WO | WO03060882 | 7/2003 |
| WO | WO03064998 | 8/2003 |
| WO | WO03102559 | 12/2003 |
| WO | WO2004003891 | 1/2004 |
| WO | WO2004003932 | 1/2004 |
| WO | WO2004032118 | 4/2004 |
| WO | WO2004107323 | 12/2004 |
| WO | WO2005045815 | 5/2005 |
| WO | WO2007024829 | 3/2007 |
| WO | WO2007073107 | 6/2007 |
| WO | WO2007091097 | 8/2007 |
| WO | WO2008057000 | 5/2008 |
| WO | WO2008060172 | 5/2008 |
| WO | WO2008/080049 | 7/2008 |
| WO | WO2008106782 | 9/2008 |
| WO | WO2010047609 | 4/2010 |
| WO | WO2010059736 | 5/2010 |
| WO | WO2010077159 | 7/2010 |

OTHER PUBLICATIONS

International Search Report for International Application No. PCT/PT2009/000055 dated Apr. 7, 2010 and Great Britain Search Report for GB Application No. 0819508.3 dated Feb. 26, 2009.
Schomburg et al, "Microfluidic components in LIGA technique" J. Micromech. Microeng. vol. 4, pp. 186-191 (1994).
Ducree et al., "The Centrifugal microfluidic Bio-Disk platform," J. Micromech. Microeng. vol. 17, pp. S103-S115 (2007).
Furlan et al., "Behavior of microfludic amplifiers" Sensors and Actuators. vol. 51, pp. 239-246 (1996).
Furlan et al., "Comparison of Wall Attachment and Jet Deflection Microfluidic Amplifiers" Micro Electro Mechanical Systems, 1996, MEMS '96, Proceedings an Investigation of Micro Structures, Sensors, Actuators, Machines and Systems, IEEE The 9th Annual International Workshop. San Diego, CA pp. 372-377 (Feb. 11, 1996).
Grumann et al., "Batch-Mode Mixing on Centrifugal Microfluidic Platforms", Lab Chip. 2005. pp. 560-565. vol. 5.
Haeberle et al., "Centrifugal Micromixer", Chem. Eng. Technology. pp. 613-616. vol. 28, No. 5 (2005).
Sudarsan et al., "Multivortex Micromixing", Artie McFerrin Department of Chemical Engineering. vol. 103, No. 19. pp. 7228-7233. (2006).
Nguyen et al., "Micromixers—A Review", Institute of Physics Publishing. Journal of Micromechanics and Microengineering.vol. 15. pp. R1-R-16. (2005).
GB Combined Search and Examination Report for Application No. GB0823660.6 dated May 18, 2009.
GB Response to Search Report for Application No. GB0823660.6 dated Dec. 13, 2010.
International Search Report and Written Opinion for International Application No. PCT/PT2009/000081 dated May 10, 2010.
Homola et al., "Surface plasmon resonance sensors: review, "Sensors and Actuators B. Elsevier Science S.A., vol. 54, No. 1, pp. 3-15 (Jan. 25, 1999).
Homola, "Present and Future of Surface Plasmon Resonance Biosensors" Anal. Bioanal Chem 377, 528-539 (2003).

(56) References Cited

OTHER PUBLICATIONS

Zoval and Madou, "Centrifuge-Based Fluidic Platforms" Proceedings of the IEEE 92, No. 1, pp. 140-153 (Jan. 2004).

Duffy et al., Microfabricated Centrifugal Microfluidic Systems: Characterization and Multiple Enzymatic Assays, Anal. Chem. American Chemcial Society. vol. 71, No. 20. pp. 4669-4678. Oct. 15, 1999.

Felton, "CD Simplicity" Anal. Chemc 75, 302A-306A Jul. 1, 2003.

Fontana, "Theoretical and Experimental Study of the surface plasmon resonance effect on a recordable compact disk", Applied Optics. vol. 43, No. 7B pp. 79-87 Jan. 1, 2004.

Chiu et al.,Calculation of Surface Plasmon Effect on Optical Discs, Jap. J. Appl. Phys. Part 1, vol. 43, No. 7B, pp. 4730-4735 (2004).

Brenner et al., "Frequency-dependent transversal flow control in centrifuge microfluidics" The Royal Society of Chemistry. Lab on Chip, 5(2): 146-150 (2005).

Application and File History for U.S. Appl. No. 13/125,777, filed Aug. 12, 2011, inventors Da Fonseca et al.

Application and File History for U.S. Appl. No. 13/143,070, filed Sep. 28, 2011, inventors Da Fonseca et al.

Application and File History for U.S. Appl. No. 12/513,927, filed Sep. 2, 2009 inventor Da Fonseca.

Application and File History for U.S. Appl. No. 13/638,378 inventor Da Fonscea.

International Search Report for International Application No. PCT/PT2011/000009 dated Oct. 18, 2011.

Japanese Notification for Refusal for Japanese Application No. 2012-545894 dispatch date Mar. 4, 2014. English Translation Provided.

International Report on Patentability for PCT/PT2009/000055 issued Apr. 26, 2011.

International Search Report for International Application No. PCT/EP2012/074874 dated Apr. 11, 2013.

* cited by examiner

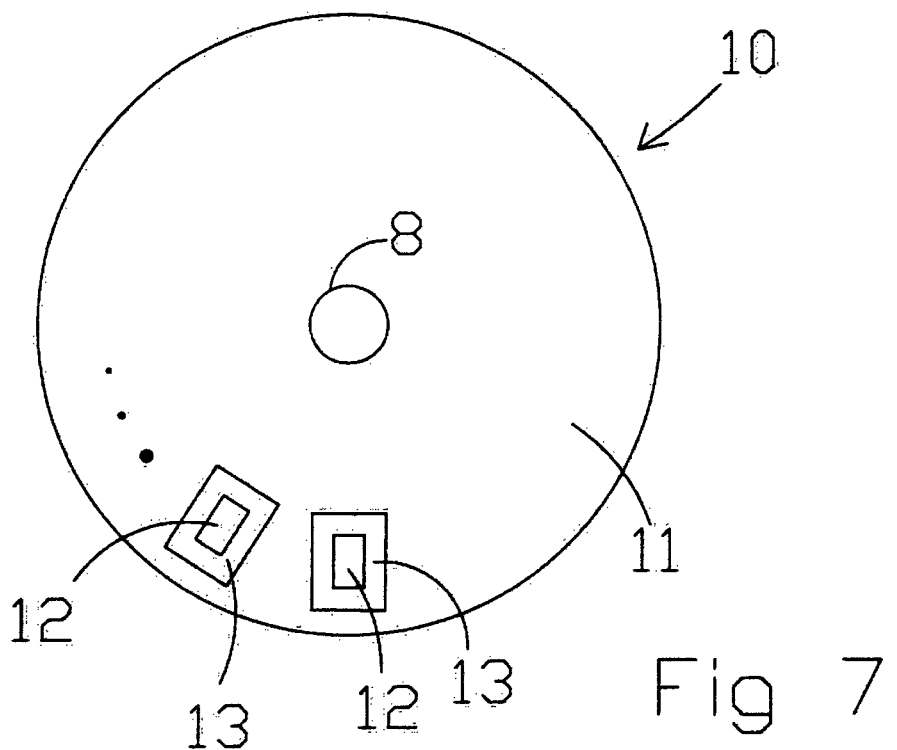
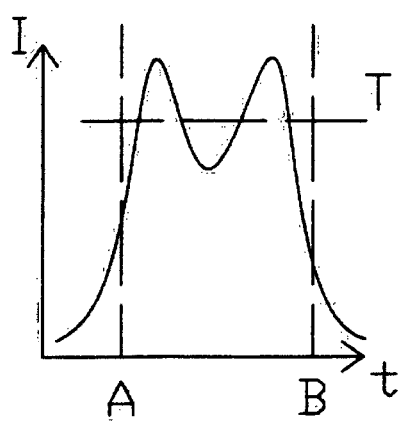
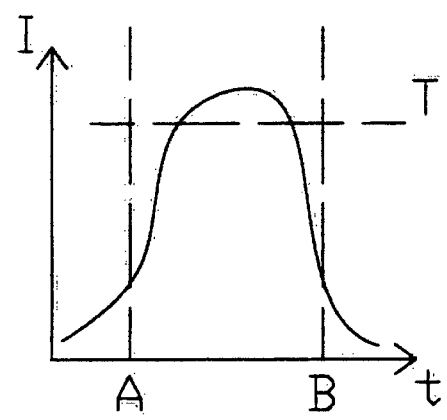

SURFACE PLASMON RESONANCE DETECTION SYSTEM

RELATED APPLICATIONS

The present application is a National Phase entry of PCT Application No. PCT/PT2010/000055, filed Dec. 7, 2010, which claims priority from Great Britain Application No. 0922440.3, filed December 2009, the disclosures of which are hereby incorporated by reference in their entireties.

FIELD OF THE INVENTION

The present invention relates to a system for detecting the presence of an analyte in a detection portion of a substrate and in particular, although not exclusively, the detection of analyte in a "lab on a disk" system using the Surface Plasmon Resonance effect.

BACKGROUND

The integration of a plurality of functions such as sample handling, treatment and analysis is an important aspect of present trends in the provision of integrated analysis of samples such as blood samples, for example in point of care analysis services. Microfluidic devices provide for sample handling and treatment in miniaturised integrated platforms through channels and other sample handling features with smallest dimensions of the order of less than 1 mm, more specifically less than 0.1 mm. Centrifugal microfluidic devices or "lab on a disk" devices are particularly promising as they do not require external pumps or other connections but can be designed to carry out a multitude of sample handling and treatment functions controlled purely by a sequence of rotational frequencies of the device.

For a fully integrated point of care (or other) analysis system a detection or analysis functionality must also be built into the device. One possibility is to provide an optical window to a detection zone of the device where an assay for target molecules in the sample being handled is carried out. For example, the detection zone can be provided with antibodies immobilized in the detection zone so that a target protein/antigen will bind to the immobilized antibodies to be retained in the detection zone. The immobilized target molecules can then be detected using optical detection methods, for example by detecting fluorescence if target molecules have previously been labelled with fluorescent dye.

One particularly interesting detection method is based on the Surface Plasmon Resonance (SPR) effect, which does not require the target molecules to be labelled. Briefly, the antibodies (or other probe molecules) are immobilized on a specialized detection surface (typically a thin metal surface coated onto a prism or a metal coated diffraction grating). Light from a light source such as a laser or a light emitting diode (LED) with or without spectral filtering is directed to the detection surface in a carefully controlled manner so that most of the energy of the incident light is absorbed by surface plasmons in the detection surface.

The SPR interaction is dependent on the relative refractive indices of the detection surface and its immediate surroundings. The binding of target molecules to the probes changes the refractive index in the immediate vicinity of the detection surface thereby changing the settings of the incident light beam at which SPR occurs. These settings include, for example, wavelength or angle of incidence. By detecting the light received from the detection surface, the presence of target molecules bound to probe molecules in the detection zone can be detected by a change in the intensity of received light, a change in the angle of incidence at which maximum absorption (resonance) occurs or a change of the wavelength at which this occurs. Alternative known methods detect corresponding changes related to the phase of the received light.

Microfluidic SPR based "lab on a disk" detection devices are described in WO-A-2008/057000, providing a detailed description of the target/probe binding, the SPR detection mechanism and its implementation in a "lab on a disk" microfluidic device using a grating as a detection surface.

JP2004/117048 describes a SPR detection system in a prism configuration using a rotating disk. Another rotating disk SPR detection system based on the prism configuration is described in WO/03102559. A characterization of SPR on rotating disk substrates has been provided by Fontana, E, Applied Optics 43, 79-87, (2004) and Chiu, K P et. al. Jap. J. appl. Phys. Part 1 43, 4730-4735 (2004). Detection systems using detection areas in a rotating support with other detection mechanisms are described in U.S. Pat. No. 5,994,150, US2001031503, U.S. Pat. No. 6,653,152, U.S. Pat. No. 6,277,653 and WO9721090. All references referred to above are hereby incorporated by reference herein.

Typically, a microfluidic "lab on a disk" substrate (as used herein to refer to a substrate arranged for microfluidic handling of fluids using the centrifugal force by rotating the substrate) is placed in a compact disc (CD) like reader device for controlled rotation of the substrate. The reader comprises an optical detection module with a light source and detector to detect an optical signal from a detection zone of the substrate.

The detection module receives light from the substrate while the substrate and detection module move relative to each other and can measure and store an intensity profile over the substrate surface. More detailed information can be captured and stored if acquisition is limited to the detection zone(s). To accomplish this, the detection module and detection zone must be appropriately aligned when signal acquisition occurs. This can be achieved in a number of ways, for example by mechanical coding between the substrate and a driving element of the reader so that the orientation of the substrate in the reader can be known if the position of the driving element can be measured or by providing a separate trigger mark on the substrate which can be detected by a separate trigger system to indicate that the detection zone is aligned with the detection module and trigger data acquisition. These approaches have a number of drawbacks in that the alignment between the mechanical coding or trigger mark and the detection zone must be highly accurate to provide precise triggering of data acquisition. This is particularly important in SPR detecting systems which rely on a careful alignment between the detection module and the detection zone in particular when the detection zone is small and even more so in multiplexed systems having a plurality of small detection zones. Moreover, these approaches require additional components and modifications of conventional CD like reader systems, thus increasing overall system costs.

SUMMARY

Embodiments of the invention provide a system for detecting and/or measuring a signal representative of the occurrence of SPR on a substrate. The substrate has a detection portion for receiving incident optical radiation for interaction with an analyte delivered to the detection zone by the microfluidic system and another portion, adjacent, for example, the detection portion. The detection and other portions may have different reflectances or transmittances for the optical radiation. The system comprises source means for illuminating a portion of the substrate with optical radiation, detector means for detecting optical radiation received, for example reflected, from the illuminated portion of the substrate and means for moving the source means and substrate relative to each other such that the illuminated portion moves from the other portion to the detection portion. The system further comprises trigger means coupled to the detector means for determining, for example, a reflectance signal indicative of the reflectance of the illuminated portion from the reflected optical radiation and for determining a trigger signal indicative of the reflectance (or transmittance) signal meeting a condition. More generally, the trigger signal is indicative of the occurrence of SPR at the detection zone. The system comprises means for triggering data acquisition from the detector arrangement in response to the trigger signal. The system may comprise means for detecting the presence of an analyte from the data based on a spatial distribution of the intensity of the received optical radiation, an angle at which a minimum of the intensity occurs or a wavelength at which a minimum of the intensity occurs.

Advantageously, by using the same reflected (or transmitted, or a diffracted order of) optical radiation which is used for data acquisition to trigger data acquisition, the need for additional components as described above is obviated and there is thus no need to ensure correct alignment between these additional components and the detection portion. The system thus provides data acquisition triggering with increased accuracy, at the same time reducing system complexity and cost.

The condition may be that the reflectance or transmittance signal drops below a threshold characteristic of the occurrence of SPR and the data acquisition means may be arranged to capture and/or measure a corresponding SPR signal. The condition that the reflectance or transmittance signal drops below a threshold is inherently met for SPR detection, which relies on changes in resonant absorption of the detected signal.

The detector means may comprise a first detector coupled to the triggering means and a second detector coupled to data acquisition means, such that the respective characteristics of the detectors can be adopted for the respective tasks of triggering data acquisition and data acquisition itself. For example, the first detector may have a faster response time than the second detector.

The detector means may include a beam splitter defining a first radiation path to the first detector and a second radiation path to the second detector, for example placing the first detector in the transmitted light path and the second detector in the reflected light path. The beam splitter may be arranged to direct more light to the second detector than the first one, preferably directing about 90% or more to the second detector, thus reducing the impact in SPR signal intensity.

Alternatively, in a grating based SPR system (using a diffraction grating for momentum matching between incoming photons and surface plasmons in the grating metal layer) different beams may be used for triggering and data acquisition, for example one of reflected, transmitted zero or higher order diffracted beams for triggering and another one of these beams for data acquisition. In this way, the flexibility of placing the detectors is increased.

The system may further comprise an information reading means coupled to the trigger means to receive the reflectance signal and to decode information contained in the temporal variation of the reflectance signal as the illuminated portion moves over the other portion. The information reading means may be arranged to start decoding information in response to a signal indicative of the reflectance signal (or other received intensity related signal) not meeting a condition indicative of SPR occurring or, additionally meeting a further condition, for example the reflective signal being within a range of values or exceeding a threshold.

The means for moving the substrate may be arranged to rotate the substrate, such as in the case of a "lab on a disk" substrate.

Further embodiments of the invention provide a substrate for use with a system as described above, the substrate comprising a detection zone arranged for optical detection of an analyte and a surrounding zone surrounding the detection zone and including an information zone which has a spatially varying reflectance profile encoding information.

Yet further embodiments provide a substrate for use with a system as described above, the substrate comprising a detection portion arranged for detection of an analyte present in the detection portion by surface plasmon resonance caused by incident optical radiation. The substrate further comprises a layer, having a first reflectance or transmittance, secured to the substrate, the layer defining a window around the detection zone exposing a portion of the substrate having a second, higher, reflectance or transmittance.

The substrate may define an axis of rotation and have a circumferentially varying reflectance profile. The detection zone and the circumferentially varying reflectance profile may be provided on a common circumference so that the information may be read without displacing the detector means from a radial position where data is acquired. In particular, where a plurality of detection zones is provided on the substrate, this provides a convenient way of associating information specific to a particular detection zone with that detection zone.

The detection zone may be arranged for detecting the presence of analyte using the Surface Plasmon Resonance effect and the substrate may define microfluidic elements for handling or manipulating a sample as it is transported from a sample reservoir to the detection zone.

BRIEF DESCRIPTION OF THE DRAWINGS

Embodiments of the invention are now described by way of example only and with reference to the accompanying drawings in which:

FIGS. 7, 8 and 9 illustrate an embodiment of a "lab on a disk" substrate where SPR occurrence is used as control method for validating the trigger signal.

DETAILED DESCRIPTION

Figure 1:
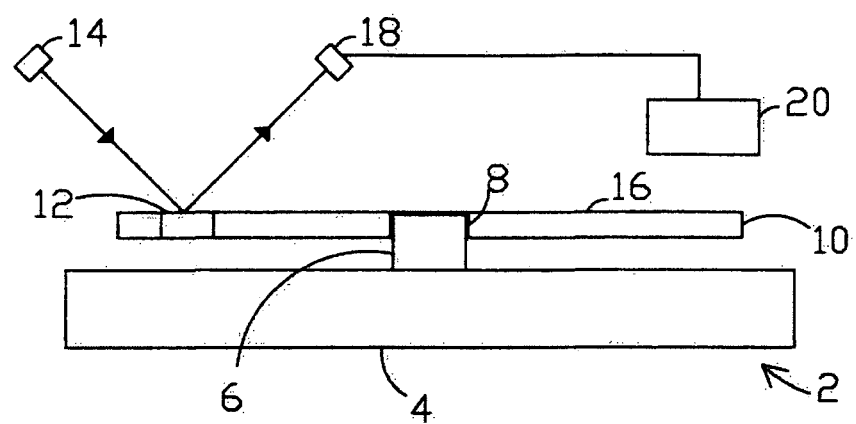
FIG. 1 schematically depicts a detection system for detecting the presence of an analyte in a "lab on a disk" substrate.

With reference to FIG. 1, a detection system comprises a driving arrangement 2. The driving arrangement comprises an electric drive 4 including control circuitry (not shown) coupled to a drive shaft 6 which is arranged to engage a corresponding cut out 8 of a "lab on a disk" substrate 10. The substrate 10 defines a detection zone 12 which is arranged to immobilize target molecules or analyte present in a sample applied to the substrate 10 on a metallic detection surface, for example a metal, such as gold, coated diffraction grating so that it can be detected using the Surface Plasmon Resonance effect.

The system comprises a radiation source 14 for illuminating a surface 16 of the substrate facing the radiation source 14 with optical radiation. In some embodiments the radiation source includes a laser or laser diode and in others it includes a light emitting diode with or without a spectral filter. A typical monochromatic wavelength is in the range of 500 nm to 1000 nm in some embodiments, more specifically 650 nm to 800 nm in some embodiments, depending on grating period, typically in the range of 800 nm to 1700 nm, grating depth, typically between 20 and 120 nm, and metal layer thickness, typically between 30 and 120 nm.

A detector module 18, which will be described in further detail below, is arranged to receive radiation reflected from the substrate 10 and is coupled to a signal processing module 20. The radiation source 14 and detector module 18 are arranged so that the presence of analyte in the detection zone 12 can be detected using an SPR based signal such as a change in reflected intensity, a change in resonance wavelength or angle at which resonance occurs, as compared to when no analyte is present.

Figure 2:
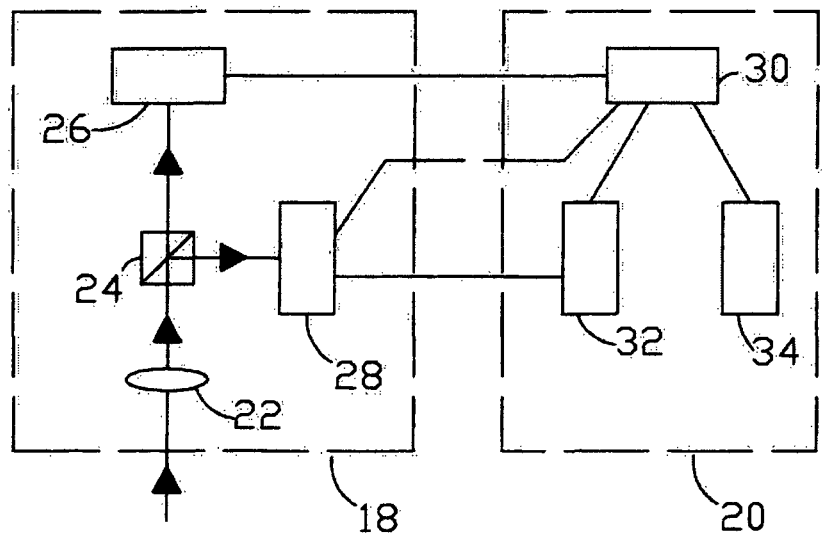
FIG. 2 schematically depicts a detection module of the system of FIG. 1.

With reference to FIG. 2, the detector module 18 comprises a lens system 22 receiving optical radiation reflected from the substrate 12 and a beam splitter 24. The beam splitter 24 receives optical radiation from the lens system 22, transmits a first portion of optical radiation to a trigger detector 26 and reflects a second portion of the received optical radiation to a data acquisition detector 28. The trigger detector 26 is coupled to a triggering module 30 and the data acquisition detector 28 is coupled to a data acquisition module 32. The trigger module 30 is coupled to the data acquisition module 32 to trigger data acquisition as will be described in more detail below and is also coupled to an information reading module 34 to trigger reading of encoded information provided on the substrate 10, again as described in detail below.

The trigger module 30 comprises circuitry for determining a signal indicative of the reflectance of the portion of the substrate 10 which is illuminated by the radiation source 14. In some embodiments, the circuitry may simply receive an intensity signal from the trigger detector 26 as the signal. In other embodiments a reflectance signal may be derived by comparing the intensity signal from the trigger detector 26 to the intensity of the radiation source 14 (which may be measured from the source 14 or a predetermined value may be used, with all transmittance and reflectance coefficients of all optical path objects considered). In other embodiments where the illuminated portion is sufficiently large, a signal may be defined as a relative reflectance by comparing the intensity at the center of the illuminated portion to the intensity at the corresponding periphery. In yet further embodiments, the trigger detector 26 may directly provide a reflectance signal to the trigger module (30).

The trigger module 30 further comprises circuitry arranged to detect whether the signal indicative of the reflectance drops below a threshold. Since the detection zone is arranged for resonant absorption of the incident light by SPR, its reflectance will be lower than that of the surrounding portions of the substrate which do not give rise to resonant absorption on the incident light. Therefore, a drop in the signal indicative of the reflectance indicates that the detection zone has come into range as the substrate rotates relative to the detector module 18 and the trigger module 30 is arranged to send a trigger signal 30 to the data acquisition module 32 when a drop in reflectance is detected (for example below a threshold value) to trigger a data acquisition. Additionally, in some embodiments, the trigger module 30 sends a trigger signal to the data acquisition detector 28 to activate it. In yet further embodiments, the trigger module 30 only sends the trigger signal to the data acquisition detector 28 which, in response starts to acquire data and sends it to the data acquisition module 32.

The respective characteristics of the trigger detector 26 and the data acquisition detector 28 are chosen for their respective tasks. In particular, substrates containing a plurality of small detection zones (for example having a circumferential width less than a millimeter or even 0.5 mm and a radial height such as 0.02 mm) require a rapid detector response with a time constant sufficiently fast to trigger data acquisition before the detection zone 12 has passed the data acquisition detector. For example, a detection zone with a circumferential dimension of 0.5 mm in a substrate spinning at 10 Hz may require a response time of less that 5 microseconds for the trigger detector 26. By contrast, a rapid response is less crucial for the acquisition detector 28 which needs a high signal to noise ratio. (Although the response time should preferably nevertheless be about 50 microseconds or less, in the example given, for a data detector of less than 5 mm in size). In embodiments where the spatial profile of intensities is detected (corresponding to an angular spread in the radiation reflected from the substrate or, with suitable spatially distributed wavelengths filtering, a wavelength spread of the reflected radiation) the data acquisition detector also requires high spatial resolution. These requirements are generally in conflict with the requirement of the fast response time of the trigger detector 28 (at least if cost-efficient components are to be used) and, accordingly, the use of two separate detectors, one as a trigger detector and the other one as a data acquisition detector, is advantageous in that it allows the characteristics of each detector to be chosen so that they are adapted for the respective tasks.

In some embodiments a charged coupled device (CCD) detector array or other photodetector array such as CMOS (Complementary Metal-Oxide Semiconductor) is used for the data acquisition detector 28 and a single photo diode detector is used for the trigger detector 26. In other embodiments the data acquisition detector 28 and data acquisition module 32 are the same, as in a FPGA (Field Programmable Gate Array) camera. In other embodiments the FPGA camera can also incorporate the trigger module 30 making this system very compact.

As mentioned above, the system includes an information reading module 34 which is arranged to decode a temporally varying profile of the reflectance signal (corresponding to a spatial profile of reflectance on the substrate as the substrate rotates relative to the detector module 18 as described below with reference to FIGS. 3 and 4) to read information, such as a serial number, a description of the probes or antibodies provided on the substrate, a code indicating the type of substrate or any other relevant information. The information reading module 34 is triggered to decode the signal indicative of the reflectance by a signal sent from the trigger module when the signal indicative of reflectance meets a condition.

In some embodiments, the condition is that the condition triggering data acquisition is not met such that information is read from the entire surface of the substrate 10, other than the detection zone 12, or at least the surface of the substrate on either side of the detection zone on the same circumference as the detection zone. In other embodiments, a further condition is imposed before the signal triggering reading of information is sent. The further condition depends on the way in which information is encoded, as discussed below.

Figure 3:
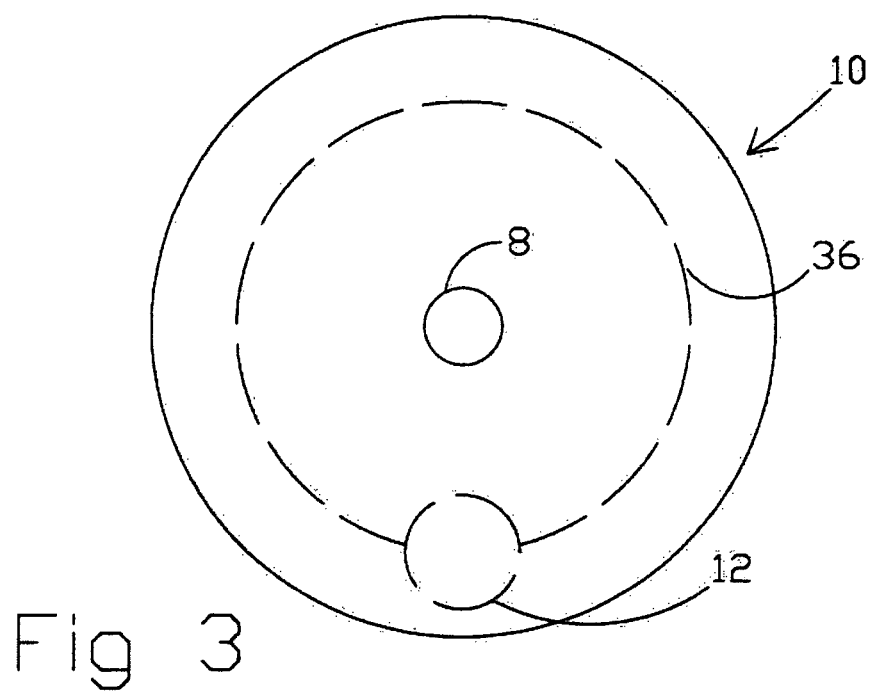
FIG. 3 schematically depicts a "lab on a disk" substrate.

With reference to FIG. 3, the substrate 10 has a track 36 of circumferentially varying reflectance on a circumference passing through the center of the detection zone 12. A circumferentially varying reflectance profile along the track 36 encodes information using a reading frame of fixed circumferential length as for conventional optical storage media such as CDs, although, in some embodiments, the reading frame is larger than that of CDs in light of the lesser information content which needs to be stored. This facilitates the manufacture of the substrate. Within the fixed reading frame, information is encoded by spatially defined pits formed in the surface 16 of the substrate 10, which result in decreased reflection of incident optical radiation as the optical radiation from the source 14 passes over the pit. A long pit encodes a binary "1" and a short pit encodes a binary "0". As the substrate rotates past the detector module 18, the spatially varying reflectance profile of the track 36 results in a temporally varying profile of received intensity at the detector module 18, with a short dip in reflectance indicating a binary "0" and a long dip in received intensity indicating a binary "1". The temporal variation in received intensity is detected by the detector module 18 and, as described above, transferred to information reading module 34, where it is decoded as for a conventional optical medium, in a manner well known to the person skilled in the art.

In the embodiment shown in FIG. 3, the information track or region extends circumferentially all the way around the substrate 10 outside the detection zone. Due to the resonant absorption in the detection zone 12, its reflectivity will be significantly lower than that of the surrounding surface including the track 36. Thus, information reading can be triggered by detecting that the condition for triggering data acquisition described above is not met. Additionally, a further condition can be imposed, for example detecting a drop in reflectivity below a second threshold, higher than that for triggering data acquisition. The same threshold may also be used to detect the binary code encoded in the track. This allows for information to be read from only a portion of the common track 36 where encoding pits are present.

In an alternative embodiment, the encoding pits described above are replaced with small silvered structures, so that information can be encoded in a spatially defined increase in reflectivity and corresponding peaks in reflectivity, the encoding otherwise being the same. In this embodiment, an additional condition for triggering the reading of information could be the reflectivity exceeding a threshold value.

In the embodiment of FIG. 3, a single detection zone 12 and track 36 are shown. In other embodiments, multiple detection zones may be provided on the substrate 10. These detection zones may be radially offset so that each detection zone has its corresponding information track 36. All the information zones may be disposed on the same circumference with a common track 36 with respective sectors of the track 36 pertaining to the detection zone which precedes it (or follows it) in the sense of rotation of the substrate within the reader. A combination of these two approaches may also be employed. For example, each sector could indicate the test corresponding to its assigned detection zone.

Figure 4:
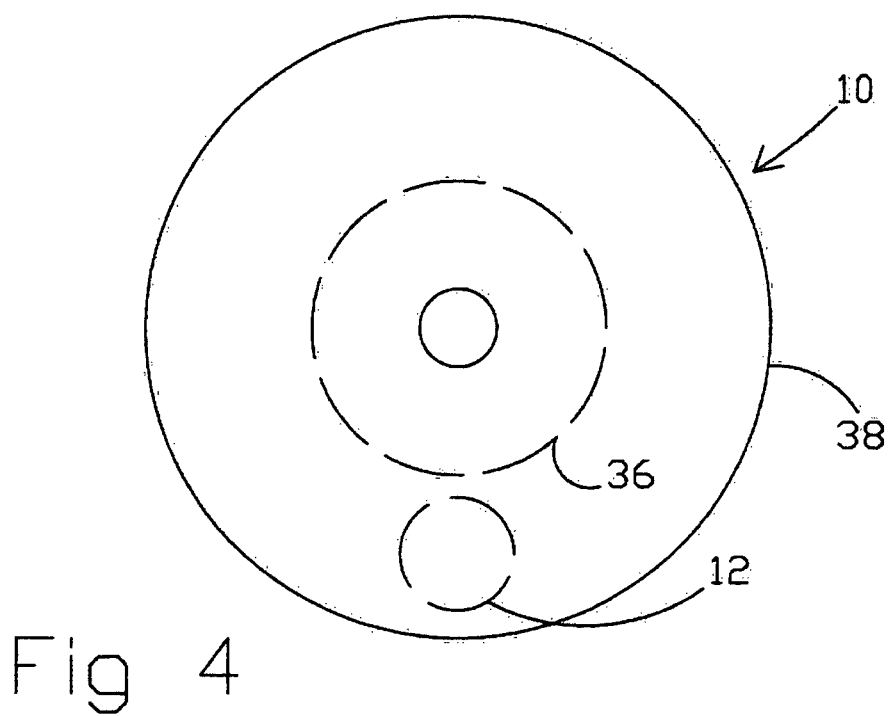
FIG. 4 schematically depicts an alternative substrate.

In yet a further embodiment, particularly applicable to one or more detection zones 12 being present in the substrate 10, the information track 36 is radially decoupled from the detection zone 12 and may be, for example, provided on a circumference radially inwards from the one or more detection zones 12, as illustrated in FIG. 4. This allows more detection zones to be placed on a circumference adjacent to the edge 38 on the substrate 10 as no space is taken up by intervening portions of the track 36. Placing more (or all) detection zones 12 on an outer circumference adjacent to the edge 38 can be desirable in certain embodiments, where this is required by the design of the microfluidic handling structures.

In the embodiments described above with reference to FIG. 3, information reading and data acquisition are multiplexed in the sense that each respective functionality is triggered as soon as the relevant condition is met. The two functionalities are separated in the embodiments described above with reference to FIG. 4 in that the detector module 18 must be radially displaced between an inner radial location for reading information and an outer radial location for data acquisition. These approaches can be combined and, for example, in the embodiments described above with reference to FIG. 3, the signal processing module 20 may be arranged such that either functionality can be operated separately. For example, an initial information reading phase as the substrate is first inserted into the reader, followed by a subsequent data acquisition phase, can be implemented.

In some embodiments, now described with reference to FIGS. 5 and 6, different beams of optical radiation received from the substrate 10, which has one or more detection surfaces in the form of a metal coated diffraction grating which both reflects and transmits incident optical radiation, are used, selecting one of a reflected or transmitted beam of a zero or lighter diffraction order.

Figure 5:
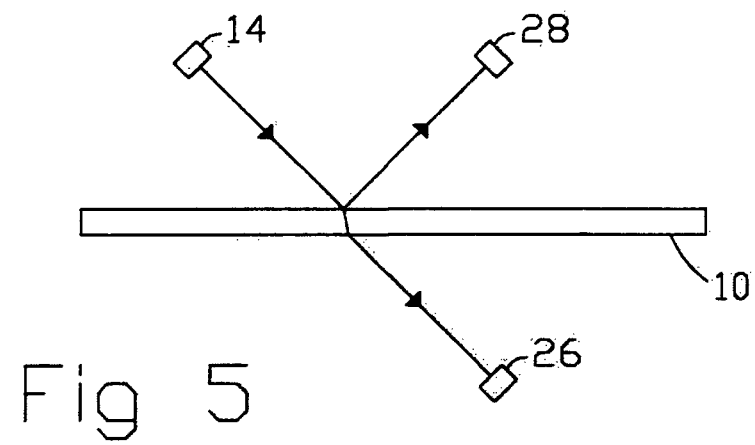
FIGS. 5 and 6 schematically depict alternative arrangements of detectors of the detection system.
Figure 6:
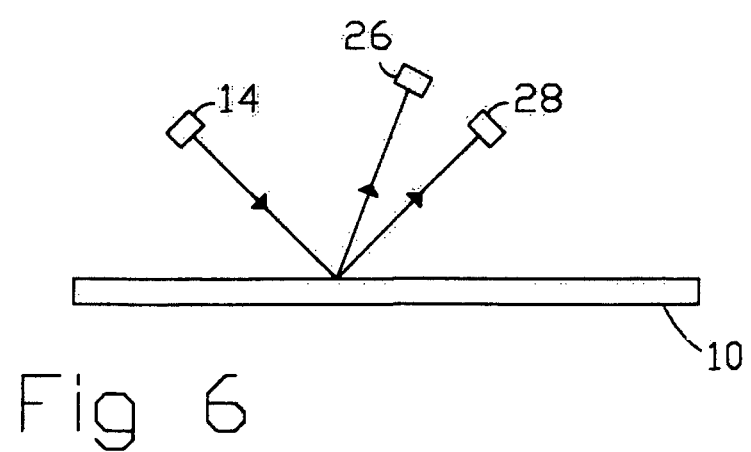

With reference to FIG. 5, the trigger detector 26 and the data acquisition detector 28 are arranged on opposite sides of the substrate 10 so that the former receives transmitted optical radiation and the latter receives reflected optical radiation, both zero diffraction order. With reference to FIG. 6, both detectors 26 and 28 are arranged on the same side of the substrate 10 to receive reflected radiation, the trigger detector 26 receiving the first (or, in some embodiments, higher) diffraction order reflected beam and the data acquisition detector 28 receiving the zero order reflection. Other embodiments use different combinations of transmitted/reflected beams of zero or higher diffraction order for the detectors 26, 28. Common to all these approaches is that different beam paths are used, thus avoiding the extra component of a beam splitter and also the associated signal attenuation.

In some embodiments using a transmitted beam path for the trigger detector 28, the information region of the substrate 10 is arranged to have a varying transmittance profile so that the trigger detector 26 is used also for reading information contained in the intensity variation of the transmitted light, as described above for the reflective case. Alternatively, some embodiments provide a separate detector for reading the information.

Various modifications of the embodiments described above are possible. For example, some embodiments have been described with detection zone(s) 12 being radially outward and the information track 36 being radially inward. Naturally, this can be reversed to accommodate specific microfluidic designs requiring a radially inward location of the detection zones. A few specific conditions for triggering data acquisition and/or information readings have been described above but it will be apparent to the skilled person that other conditions are equally feasible and may be appropriate depending on the specific implementation. For example, rather than detecting the reflectance of the substrate falling below a specified threshold (or exceeding a threshold) the condition for data acquisition, information reading or both may be defined as the reflectance lying within a given range of values.

While a fixed reading frame, length of pit (or hill) encoding of information has been described above, other ways of encoding information in a varying reflectance profile are known to the skilled person and can equally be employed.

In general terms, the system is self triggering so that, in the case of the described embodiments, a trigger signal is generated when the received optical radiation is indicative of SPR occurring in the detection zone.

This self triggering characteristic may be used to control which signals are to be measured and accepted as valid. As now described with reference to FIG. 7, in some embodiments, the substrate 10 has a non-reflective cover, for example an opaque film or label 11 secured on the illuminated surface 16. The label 11 has optical windows 13 to allow one or more detection zones 12 to be illuminated. With substrate 10 rotating at a given speed, the trigger detector 26 will acquire the profiles in FIG. 8 or in FIG. 9, as explained below.

FIG. 8 shows a signal (e.g. intensity) profile as a function of time detected when the detection zone 12 moves past the detector module 18 and SPR occurs as a result of a sample of liquid having been successfully delivered to the detection zone 12 by the microfluidic structure. The corresponding profile has two falling edges crossing a predefined threshold. SPR occurs in the detection zone 12 whenever a liquid sample is present in the detection zone 12 (the presence or not of analyte in the sample determining a more specific change of the SPR, for example a shift in the angle of resonance, as discussed above) and results in the overall temporal intensity profile at the trigger detector 26, shown in FIG. 8. By detecting this characteristic profile, for example by detecting the four threshold crossings of the signal (two rising, two falling) the trigger module 30 derives, in some embodiments, a validation signal and provides this validation signal to the data acquisition module 32, which then marks the acquisition as valid, for example by setting a flag of a corresponding data record accordingly.

FIG. 9 shows a signal profile as a function of time detected when the detection zone 12 moves past the detector module 18 and SPR does not occur (for example because of misalignment of the "lab on a disk" or because the microfluidic system failed to deliver the liquid sample to the detection zone 12). In this case, the trigger module will fail to detect the SPR profile of FIG. 8, since only two threshold crossings (one rising, one falling) will be detected. This signal is characteristic of the detector passing a detection zone 12 in a window 13 without SPR occurring. As a result of detecting such a signal, the trigger module 30 sends a invalidation signal to the data acquisition module 32 to cause it to mark the acquisition as invalid. On receiving the invalidation signal, the data acquisition module either marks an acquired data record as invalid, stores only an invalid flag as the data record, or does not acquire and store any data record at all.

In some embodiments, the trigger signal from the trigger module 30 to the acquisition module 32 is suppressed, rather than sending an invalidation signal, so that no data acquisition occurs. In some embodiments, the trigger module does not generate validation or invalidation signals but simply triggers data acquisition by sending the trigger signal if the detected signal is valid or does not trigger data acquisition if the detected signal is invalid by suppressing the trigger signal. In some embodiments, the trigger module 30 or data acquisition module 32 causes the device to alert a user that a fault has occurred. The condition for identifying a fault (or for generating the invalidation signal) may be that the predetermined threshold has been crossed (indicating a detection rather than an information zone) in the case where the intensities received from the information zone are less than those for the windows 13) and that only two threshold crossings were detected (indicating no SPR occurring).

In some embodiments, the trigger signal is generated on the first threshold crossing and a validation or invalidation signal is subsequently sent depending on whether respectively, there are three or one further threshold crossings before the signal drops below a further, lower threshold indicated that the window 13 has passed the detector. The three further threshold crossings can be detected in a number of ways, for example by detecting a single further threshold crossing from below to above the threshold or two further crossings irrespective of the direction, all being indicative of the signal crossing the threshold a further three times after the first crossing.

For substrates where various detection zones are supplied in parallel by microfluidics this provides a control check for the validity of signals acquired from the detection zones so that the data acquisition module 32 does not need to analyze whether or not the respective detection zone image is valid or not. For substrates where one or more detection zones are handled in sequence and are interconnected by sequentially microfluidic structures this provides a way to abort the entire analyte detection if an error is detected.

The embodiments described above use three separate modules, one for processing the trigger signal from trigger detector, one for data acquisition and one for reading information. However, in some embodiments, some or all of these modules may be provided in a single, hardware or software, module. If response time resolution is considered, the trigger module may advantageously incorporate the information reading module as the kind of information typically considered (serial number, analyte type, etc) can be rapidly translated by basic electronic components. This way the function of interpreting the trigger signal (induced by SPR occurrence or any of the information conditions described) from the trigger detector is handled by the trigger module and the more complex and richer SPR signal is handled by the data acquisition module. It will be understood that the different modules, in some embodiments, merely refer to a logical distinction and that all three modules may be provided both separately or on a common hardware, such as a suitably programmed microprocessor.

The signal processing module (20) may be implemented using specifically adapted hardware components for its processing circuitry, such as an ASIC, or alternatively, a multi-purpose processor with appropriate software can be used instead. A combination of these two approaches is of course equally possible.

The embodiments described above have separate, specifically adapted detectors for data acquisition of the SPR signal and acquisition triggering. This allows each detector to be adapted for the specific requirements of its respective task, as described above. However, it is equally possible to use a single detector for both functions if the characteristics of the detector (response time and resolution) are capable of accommodating the requirements of both tasks.

While specific examples of applications of the described detection system are given above, such as point of care applications and specifically, point of care analysis of blood samples, any other application requiring an integrated analysis solution can equally be addressed using the described system.

The specific description above has been made in terms of centrifugal microfluidic devices. It will be apparent to the skilled person that the invention also is applicable to other substrates moving relative to a detector, for example linearly translating substrates or rotating, drum-like or cylindrical substrates. Likewise, the invention may be useful in connection with the detection mechanisms which are not based on SPR, for example fluorescence.

The skilled person will thus appreciate that variations of the disclosed arrangements are possible without departing from the invention. Accordingly, the above description of several embodiments is made by way of example and not for the purpose of limitation. It will be clear to the skilled person that modifications can be made to the arrangements without significant changes to the operation described above. The present invention is intended to be limited only by the scope of the following claims.

For purposes of interpreting the claims for the present invention, it is expressly intended that the provisions of Section 112, sixth paragraph of 35 U.S.C. are not to be invoked unless the specific terms "means for" or "step for" are recited in the subject claim.

The invention claimed is:

1. A system for detecting changes in Surface Plasmon Resonance indicative of the presence of an analyte in a sample on a substrate, the substrate having a detection portion arranged to receive incident optical radiation for interaction with a detection surface of the detection portion when the sample is present in the detection portion, the system comprising:
a source disposed to illuminate a portion of the substrate with optical radiation, the source being arranged to cause surface plasmon resonance at the detection surface when the sample is present in the detection portion;
a detector arrangement disposed to receive optical radiation received from the illuminated portion of the substrate;
a driving arrangement arranged to couple to the substrate and move one of the source and the substrate relative to the other, such that the illuminated portion moves over the substrate to the detection portion;
a processor coupled to the detector arrangement, the processor being configured to:
generate a trigger signal indicative of Surface Plasmon Resonance occurring in the illuminated portion; and
acquire data from the detector arrangement in response to the trigger signal, wherein a change in local refractive index at the detection surface is determinable from the data.

2. The system of claim 1 wherein the detector arrangement comprises a first detector coupled to the processor and a second detector coupled to the processor, the processor being configured to:
generate the trigger signal using a signal received from the first detector, and;
acquire data using a signal from the second detector.

3. The system of claim 2 wherein the first detector has a faster response time than the second detector.

4. The system of claim 2 wherein one of the first and second detectors is arranged to receive optical radiation reflected by the substrate and the other one is arranged to receive optical radiation transmitted through the substrate.

5. The system of claim 2 wherein one of the first and second detectors is arranged to receive optical radiation of a non-zero diffracted order and the other one is arranged to receive radiation of a zero diffracted order.

6. The system of claim 2 wherein the second detector is arranged to receive zero order diffraction reflected optical radiation.

7. The system of claim 1 wherein the optical radiation received by the detector arrangement is reflected by the substrate.

8. The system of claim 1 wherein the processor is configured to detect the presence of an analyte from the data based on a change in a spatial distribution of the intensity of the received optical radiation, an angle at which a minimum of the intensity occurs or a wavelength at which a minimum of the intensity occurs.

9. The system of claim 1 wherein the processor is configured to generate the trigger signal in response to the intensity of the optical radiation received by the detector arrangement and dropping below a threshold value.

10. The system of claim 1 wherein the processor is configured to generate the trigger signal in response to the intensity of the optical radiation received by the detector arrangement and rising above a threshold.

11. The system of claim 10, wherein the processor is configured to, subsequent to generating the trigger signal, generate a validation signal indicative of the trigger signal being valid if the intensity crosses the threshold three times before dropping below a further, lower threshold.

12. The system of claim 10, wherein the processor is configured to acquire data only if a validation signal is generated subsequent to a corresponding trigger signal.

13. The system of claim 1 wherein the processor is configured to analyze a temporal waveform received from the detector arrangement to validate the occurrence of surface plasmon resonance in the illuminated portion.

14. The system of claim 1, wherein the processor is configured to decode information encoded in a spatial reflectance profile on the substrate, the processor being configured to receive a signal representative of the intensity of the received optical radiation to decode information contained in temporal variations of the signal as the illuminated portion moves over the spatial reflectance profile.

15. The system of claim 14 wherein the processor is configured to generate a further trigger signal indicative of surface plasmon resonance not occurring in the illuminated portion and to decode information in response to the further trigger signal.

16. The system of claim 15, wherein the further trigger signal is indicative of the intensity of the received optical radiation meeting a further condition.

17. The system of claim 16, wherein the further condition is the intensity exceeding a first threshold, but not a second threshold.

18. The system of claim 1 wherein the driving arrangement is arranged to rotate the substrate about an axis of rotation.

19. A system for detecting changes in intensity of optical radiation received from a substrate, the substrate having a detection portion for receiving incident optical radiation for interaction with a sample present in the detection portion, the system comprising:
a source disposed to illuminate a portion of the substrate with optical radiation, the source being arranged to cause surface plasmon resonance at the detection surface when the sample is present in the detection portion;
a detector arrangement disposed to receive optical radiation from the illuminated portion of the substrate, wherein the detector arrangement comprises a first detector and a second detector, the first detector having a faster response time than the second detector;
a driving arrangement arranged to couple to the substrate and move one of the source and the substrate relative to the other, such that the illuminated portion moves over the substrate to the detection portion;
a processor coupled to the detector arrangement, the processor being configured to:
generate a trigger signal indicative of Surface Plasmon Resonance occurring in the illuminated portion using a signal from the first detector; and
acquire data from the detector arrangement, using a signal from the second detector, in response to the trigger signal, wherein a change in local refractive index at the detection surface is determinable from the data.

* * * * *